United States Patent
Edaka et al.

(10) Patent No.: US 11,071,700 B2
(45) Date of Patent: Jul. 27, 2021

(54) COLOR INK SET FOR COSMETIC APPLICATION

(71) Applicant: FUNAI ELECTRIC CO., LTD, Osaka (JP)

(72) Inventors: Keiichi Edaka, Lexington, KY (US); Ajay K. Suthar, Lexington, KY (US)

(73) Assignee: Funai Electric Co., Ltd.

( * ) Notice: Subject to any disclaimer, the term of this patent is extended or adjusted under 35 U.S.C. 154(b) by 0 days.

(21) Appl. No.: 16/112,830

(22) Filed: Aug. 27, 2018

(65) Prior Publication Data

US 2018/0360711 A1 Dec. 20, 2018

Related U.S. Application Data

(62) Division of application No. 14/943,081, filed on Nov. 17, 2015, now abandoned.

(51) Int. Cl.
| | |
|---|---|
| A61K 8/34 | (2006.01) |
| A61Q 3/02 | (2006.01) |
| A61Q 1/02 | (2006.01) |
| A61K 8/39 | (2006.01) |
| A61K 8/46 | (2006.01) |

(52) U.S. Cl.
CPC ............... *A61K 8/345* (2013.01); *A61K 8/39* (2013.01); *A61K 8/466* (2013.01); *A61Q 1/02* (2013.01); *A61Q 3/02* (2013.01); *A61K 2800/43* (2013.01); *A61K 2800/591* (2013.01)

(58) Field of Classification Search
CPC .................................. A61K 8/345; A61Q 1/02
See application file for complete search history.

(56) References Cited

U.S. PATENT DOCUMENTS

| | | | |
|---|---|---|---|
| 5,491,502 A * | 2/1996 | Swanson | B41J 2/17513 347/87 |
| 5,529,767 A | 6/1996 | Brox et al. | |
| 5,958,121 A | 9/1999 | Lin | |
| 5,981,623 A | 11/1999 | McCain et al. | |
| 5,981,651 A | 11/1999 | Patel et al. | |
| 6,926,766 B2 | 8/2005 | Pistagna et al. | |
| 7,459,517 B2 | 12/2008 | Fukui et al. | |
| 2002/0112643 A1 | 8/2002 | Tyvoll et al. | |
| 2003/0035034 A1 | 2/2003 | Fukumoto et al. | |
| 2003/0076372 A1 | 4/2003 | Asakawa | |
| 2003/0180336 A1 * | 9/2003 | Sasaki | A61Q 5/02 424/401 |
| 2004/0078278 A1 | 4/2004 | Dauga et al. | |
| 2004/0206271 A1 | 10/2004 | Randler et al. | |
| 2006/0171909 A1 | 8/2006 | Morrissey et al. | |
| 2006/0229382 A1 | 10/2006 | Schweikart et al. | |
| 2007/0044253 A1 | 3/2007 | Kravtchenko et al. | |
| 2007/0139508 A1 * | 6/2007 | Muyskens | B41J 3/36 347/109 |
| 2007/0140998 A1 | 6/2007 | Kato et al. | |
| 2009/0075038 A1 * | 3/2009 | Butler | C09D 11/037 428/196 |
| 2011/0268873 A1 * | 11/2011 | Blette | A61K 8/40 427/147 |
| 2013/0045175 A1 * | 2/2013 | Teixeira Tagae Biaggio | A61K 8/361 424/62 |
| 2015/0042733 A1 * | 2/2015 | Aoyama | C08K 5/053 347/86 |

FOREIGN PATENT DOCUMENTS

| | | |
|---|---|---|
| EP | 1371697 A2 | 12/2003 |
| JP | 2008056607 A | 3/2008 |
| WO | 2010022377 A2 | 2/2010 |

OTHER PUBLICATIONS

Pubmed, https://pubchem.ncbi.nlm.nih.gov/compound/1_2-Benzisothiazol-3_2H_-one, 42 pgs.*
EU Scientific Committe on Consumer Safety, 1,-benzisothiazol-3-one, 32 pgs (Year: 2012).*

* cited by examiner

*Primary Examiner* — Kyle A Purdy
(74) *Attorney, Agent, or Firm* — Luedeka Neely Group, PC

(57) ABSTRACT

A cosmetic ink set, method for printing and printer containing the ink set. The ink set includes at least two of a) a cyan ink that includes a cosmetically approved cyan dye; b) a magenta ink that includes a cosmetically approved magenta dye; and c) a yellow ink that includes a cosmetically approved yellow dye. Each of the cyan ink, magenta ink and yellow ink contains 1) a cosmetically approved humectant; 2) a cosmetically approved surfactant; and 3) water in an amount sufficient to provide 100 wt. % for each of the cyan, magenta and yellow inks based on a total weight of the ink.

6 Claims, 1 Drawing Sheet

COLOR INK SET FOR COSMETIC APPLICATION

RELATED APPLICATION

This application is a division of application Ser. No. 14/943,081, filed Nov. 17, 2015, now pending.

TECHNICAL FIELD

The disclosure is directed to an ink set for printing full color images intended for cosmetic applications and in particular an ink set for full color printing that includes cosmetically approved cyan, magenta, and yellow dyes and ink composition components.

BACKGROUND AND SUMMARY

Current colorants and ink formulation materials are not on a list of approved chemicals for use in cosmetic applications; thus making current inks unacceptable for use as cosmetic inks. Traditional ink jet inks include a carrier fluid, a humectant that may include water-soluble or organic solvents, a dye or pigment, surface active agents, and other ingredients. Traditional inks have been optimized for application to various substrates, including porous and non-porous surfaces, while maintaining a color spectrum defined by the L*a*b* values of the individual inks.

The L*a*B* values are defined by the Commission Internationale de l'Eclairage (CIE) and were modeled after a color-opponent theory stating that two colors cannot be red and green at the same time or yellow and blue at the same time. L* indicates lightness, a* is the red/green coordinate, and b* is the yellow/blue coordinate. Deltas for L* ($\Delta L^*$), a* ($\Delta a^*$) and b* ($\Delta b^*$) may be positive (+) or negative (−). The total difference, Delta E ($\Delta E^*$), however, is always positive. Accordingly, $\Delta L^*$ (L* sample minus L* standard)=difference in lightness and darkness (+=lighter, −=darker); $\Delta a^*$ (a* sample minus a* standard)=difference in red and green (+=redder, −=greener); $\Delta b^*$ (b* sample minus b* standard)=difference in yellow and blue (+=yellower, −=bluer); and $\Delta E^*$=total color difference. In order to determine the total color difference between all three coordinates, the following formula is used:

$$\Delta E^* = [\Delta L^{*2} + \Delta a^{*2} + \Delta b^{*2}]1/2.$$

Slight changes in ink formulations may provide dramatic changes in the L*a*b* values of the primary colors, cyan, magenta, and yellow as well as other properties of the inks. For example, formulation changes may affect the jetting properties of the inks including the viscosity, droplet size, droplet velocity, drying time, color fastness, and banding and/or graininess of images printed with the inks. While ink jet inks have been formulated for use in business and home printing applications to meet the foregoing requirements, such inks cannot be used for printing on human nails or skin. Many of the ingredients used in conventional inks are not approved for such applications.

Furthermore, not all cosmetically approved compositions that can be used in inks will provide suitable thermal ink jet ink compositions that are equivalent in performance to conventional ink jet inks. Accordingly, there is a need to provide ink jet ink formulations and ink sets that meet cosmetic standards while maintaining traditional print quality and printing reliability standards.

In view of the foregoing, an embodiment of the disclosure provides a cosmetic ink set for thermal ink jet printing. The cosmetic ink set includes at least two of a) a cyan ink that includes a cosmetically approved cyan dye in an amount ranging from about 1 to about 6 wt. % based on a total weight of the cyan ink; b) a magenta ink that includes a cosmetically approved magenta dye in an amount ranging from about 1 to about 6 wt. % based on a total weight of the magenta ink; and c) a yellow ink that includes a cosmetically approved yellow dye in an amount ranging from about 1 to about 6 wt. % based on a total weight of the yellow ink. Each of the cyan ink, magenta ink and yellow ink contains: a cosmetically approved humectant in an amount ranging from about 7 to about 30 wt. % based on a total weight of the ink; a cosmetically approved surfactant in an amount ranging from about 0.05 to about 5.0 wt. % based on a total weight of the ink; and water in an amount sufficient to provide 100 wt. % for each of the cyan, magenta and yellow inks based on a total weight of the ink.

Another embodiment provides a method of printing with cosmetic inks on human nails and skin. The method includes providing an ink jet pen and an ink set for full color thermal ink jet printing, the ink set includes a) a cyan ink that includes a cosmetically approved cyan dye in an amount ranging from about 1 to about 6 wt. % based on a total weight of the cyan ink; b) a magenta ink that includes a cosmetically approved magenta dye in an amount ranging from about 1 to about 6 wt. % based on a total weight of the magenta ink; and c) a yellow ink that includes a cosmetically approved yellow dye in an amount ranging from about 1 to about 6 wt. % based on a total weight of the yellow ink. Each of the cyan ink, magenta ink and yellow ink contains a cosmetically approved humectant in an amount ranging from about 7 to about 30 wt. % based on a total weight of the ink; a cosmetically approved surfactant in an amount ranging from about 0.08 to about 5.0 wt. % based on a total weight of the ink; and water in an amount based on a total weight of the ink sufficient to provide 100 wt. % for each of the cyan, magenta and yellow inks based on a total weight of the ink. The ink set is ejected in a predetermined amount onto the skin, finger nails or toe nails of a person.

A further embodiment of the disclosure provides an ink jet pen that includes a cyan, magenta and yellow ink set for full color printing on humans. The ink jet pen contains a) a cyan ink comprising a cosmetically approved cyan dye in an amount ranging from about 1 to about 6 wt. % based on a total weight of the cyan ink; b) a magenta ink comprising a cosmetically approved magenta dye in an amount ranging from about 1 to about 6 wt. % based on a total weight of the magenta ink; and c) a yellow ink comprising a cosmetically approved yellow dye in an amount ranging from about 1 to about 6 wt. % based on a total weight of the ink. Each of the cyan ink, magenta ink and yellow ink contains: a cosmetically approved humectant in an amount ranging from about 7 to about 30 wt. % based on a total weight of the ink; a cosmetically approved surfactant in an amount ranging from about 0.05 to about 5.0 wt. % based on a total weight of the ink; and water in an amount sufficient to provide 100 wt. % for each of the cyan, magenta and yellow inks based on a total weight of the ink.

An advantage of the foregoing embodiments is that the disclosure provides ink sets that may be used to provide a full spectrum of colors for use in cosmetic applications. The ink sets may be used in a micro-fluid ejection head thereby providing more precise control of the ink color that is printed and more precise placement of ink on skin, finger nail, toe nails, etc. The ink set may also be suitable for improved color matching while maintaining low banding and graininess printing scores. Other features and advantages of the disclosed embodiments may be evident by reference to the following disclosure.

BRIEF DESCRIPTION OF THE DRAWINGS

Further advantages of the embodiments will become apparent by reference to the detailed description of exemplary embodiments when considered in conjunction with the drawings, wherein like reference characters designate like or similar elements throughout the several drawings as follows.

DETAILED DESCRIPTION OF EXEMPLARY EMBODIMENTS

Figure 1:
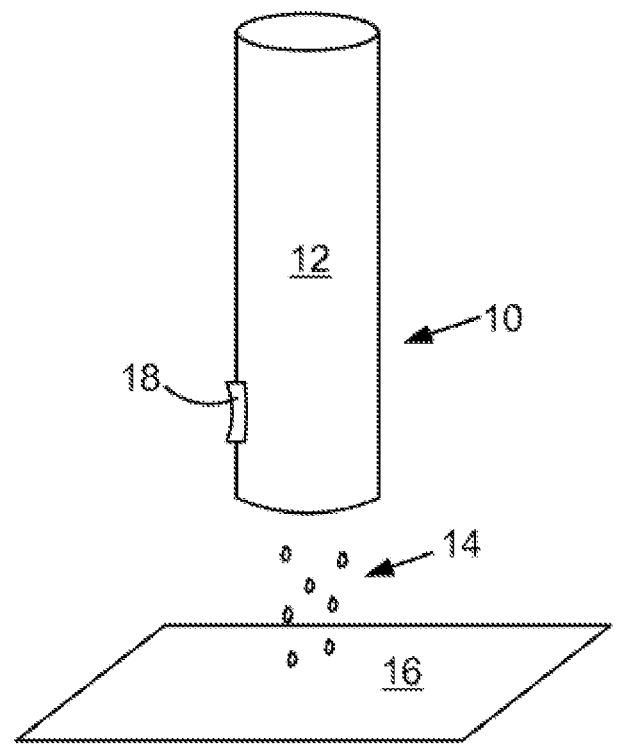
FIG. 1 is a perspective view, not to scale, of a hand held cosmetic ink jet printing device.
Figure 2:
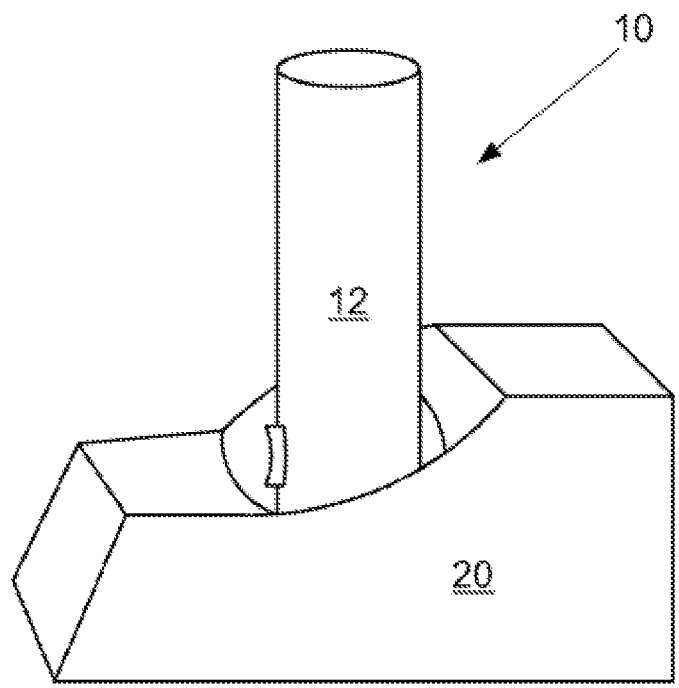
FIG. 2 is a perspective view, not to scale, of a maintenance station for the cosmetic ink jet printing device of FIG. 1.

Embodiments of the disclosure provide, for the first time, a full color ink set and hand held ink jet printer that includes only cosmetically approved ink ingredients. The formulation is specifically adapted for use with a thermal ink jet printer and can substantially match traditional print quality and thermal ink jet printing reliability. The quality and reliability of the cosmetically suitable ink formulations may be determined using various comparisons to traditional ink jet inks, such as graininess, banding, and color gamut.

Accordingly, it was necessary to identify certain cosmetic grade colorants to determine if any such colorants could be used to match traditional ink jet ink colorants. Only the basic cyan, magenta and yellow colorants were sought as all other colors could be produced from a combination of these colorants. The colorants had to not only be comparable to the traditional ink jet ink colorants, they also had to be compatible with other ink components including humectants, surfactants, solvents, and the like.

Suitable colorants may be selected from cosmetic grade dyes or pigments, with cosmetic or food grade dyes being particularly suitable for making a full color ink set according to the disclosure. Of the available cosmetic grade colorants, the following colorants were identified as useful for making ink jet formulations according to the disclosure.

The blue dyes may be selected from benzenemethanaminium, N-ethyl-N-[4-[[4-[[ethyl](3-sulfophenyl) methyl]amino]phenyl](4-hydroxy-2-sulfophenyl)methylene]-2,5-cyclo-hexadien-1-ylidene]-3-sulfo-,inner salt, disodium salt (FOOD BLUE 2); sodium 1-amino-9,10-dioxo-4-phenylaminoanthracene-2-sulphonate (ACID BLUE 5); benzenemethanaminium, N-ethyl-N-[4-[[4-[ethyl [(3-sulfophenyl)methyl]amino]phenyl](2-sulfophenyl) methylene]-2,5-cy-clohexadien-1-ylidene]-3-sulfo-, inner salt, diammonium salt (ACID BLUE 9); and benzenemethanaminium,N-[4-[[4-[(4-ethoxyphenyl)amino]phenyl][4-[ethyl[(3-sulfophenyl)-methyl]amin]-2-methylphenyl]methylene]-3-methyl-2,5-cyclohexadien-1-ylidene]-N-ethyl-3-sulfo-, inner salt, monosodium salt (BRILLIANT BLUE).

The red dyes may be selected from 1-(2,4-xylylazo)-2-naphthol-3,6-disulphonic acid disodium salt (ACID RED 26); trisodium 3-hydroxy-4-(4-sulfonato-1-naphthylazo)-2, 7-naphthalenedisulfonate (ACID RED 27); 7-naphthalenedisulfonicacid,4-amino-5-hydroxy-6-phenylazo-disodium salt (ACID RED 33); sulforhodamine B monosodium salt (ACID RED 52); 2-(2,4,5,7-tetrabromo-6-hydroxy-3-oxo-3h-xanthen-9-yl)-benzoic acid disodium (ACID RED 87); 2',4',5',7'-tetrabromo-4,5,6,7-tetrachloro-fluoresceidisodium salt (ACID RED 92); 4,5,6,7-tetrachloro-2',4',5',7'-tetraiodo-fluoresceidisodium salt (ACID RED 94); and xanthylium,9-(2-carboxyphenyl)-3-[(2-methylphenyl)amino]-6-[(2-methyl-4-sulfophenyl)amino]-hydroxide, inner salt, monosodium salt (ACID VIOLET 9).

The yellow dyes may be selected from 2,4-dinitro-1-naphthol-7-sulfo disodium salt (ACID YELLOW 1); benzenesulfonic acid, 4-4,5-dihydro-3-methyl-5-oxo-4-(phenylazo)-1H-pyrazol-1-yl-,sodium salt (ACID YELLOW 11); 1H-Pyrazole-3-carboxylic acid, 4,5-dihydro-5-oxo-1-(4-sulfophenyl)-4-[(4-sulfophenyl)azo]-,trisodium salt (ACID YELLOW 23); Sodium 5-chloro-2-(5-hydroxy-3-methyl-4-(4-((4-methylphenyl)sulphonyloxy)phenylazo)-pyrazol-1-yl)benzenesulphonate (ACID YELLOW 40); and 9-(o-carboxyphenyl)-6-hydroxy-3h-xanthen-3-one,disodiumsalt (ACID YELLOW 73).

Each of the foregoing dyes must not only be compatible with other ingredients in the inks, but must also be compatible with one another and provide color match reproduction, jetting ability, and jetting reliability that is equal to or better than traditional ink jet ink sets. Accordingly, was necessary to consider the solubility of the dye in the ink formulation, the viscosity of the resulting ink formulation, the drying time of the ink formulation on skin or nails, and the surface tension of the ink formulation on skin or nails.

Water soluble dyes are dyes that are substantially soluble in aqueous solutions. Such dyes include acid dyes which are dyes that contain acidic groups, such as sulphonic acid groups. The amount of cyan, magenta and yellow dyes in each ink formulation may range from about 1 to about 6 wt. % base on a total weight of each of the ink formulations. A typical amount of dye in each ink formulation may range from about 2 to about 4 percent by weight based on a total weight of the ink formulation.

Another component of the ink formulations described herein is one or more humectants. The humectants, like the dyes described above, are cosmetically approved humectants. Humectants are hydrophilic compounds that are used to keep the formulations from drying out too quickly on the ejection heads. Suitable cosmetically improved humectants include, but are not limited to, polyhydroxy compounds such as 1,2-propanediol, 1,3-propandiol, dipropylene glycol, glycerol, polyethylene glycol, polypropylene glycol, polybutylene glycol, and mixtures thereof. The amount of humectant in each ink formulation may range from about 7 to about 30% by weight based on a total weight of the ink formulation. A typical ink formulation may contain from about 15 to about 25 wt. % humectant based on a total weight of the ink formulation.

A minor amount of penetrant may be used in each of the ink formulations described above. The penetrant is added to the ink compositions to improve penetration by the ink drops into the surface of a substrate and to reduce or eliminate intercolor bleeding (i.e., lateral bleeding of color). Penetrants for use in the compositions described herein may include 1,2 alkyl diols containing from 4 to 10 carbon atoms in the alkyl group. Suitable cosmetically approved penetrants may be selected from 1,2-hexanediol, 1,2-pentanediol, and mixtures thereof. The penetrant is present in the ink composition in an amount of from between about 0.05 to about 5% by weight based on a total weight of the ink composition. A desirable amount of penetrant in each of the ink formulations may range from about 1 to about 4 percent by weight based on a total weight of the ink formulation.

Another component of the ink formulations described herein is a cosmetically approved nonionic surfactant. The surfactant is included in the ink formulation in order to reduce the evaporation rate of components of the ink formulation in order to increase the decap time for the ink jet print head and to aid in cleaning the ink jet print head between printing cycles. Such surfactants include, but are not limited to polyoxyethylene sorbitan monolaurate, polyoxyethylene sorbitan monostearate, polyoxyethylene sorbitan monooleate, N-(coconut oil acyl)-N-methyltaurine sodium salt, and 1,4-bis(2-ethylhexyl)-sodium sulfosuccinate. The amount of surfactant in each of the ink formulations described above may range from about 1 to about 3 wt. % base on a total weight of the ink formulation.

Each of the components described above are water soluble components of the ink formulations. Accordingly, a major component of each of the ink formulations described above is water. Deionized water is preferred and the amount of water may range from about 50 to about 90 percent by weight based on a total weight of the ink formulation. A typical amount of water in each of the ink formulations may range from about 60 to about 80 percent by weight based on a total weight of the ink formulation.

Exemplary non-limiting ink formulations are provided in the following table.

TABLE 1

|  |  | Wt. % |  | Wt. % |  | Wt. % |
|---|---|---|---|---|---|---|
| Colorant | Blue Dye | 3.0 | Red Dye 1 | 1.7 | Yellow Dye | 3.5 |
|  |  |  | Red Dye 2 | 0.8 |  |  |
| Humectants | 1,2-propanediol | 7.0 | 1,2-propanediol | 7.0 | 1,2-propanediol | 7.0 |
|  | 1,3-propanediol | 7.0 | 1,3-propanediol | 7.0 | 1,3-propanediol | 7.0 |
|  | Dipropylene glycol | 6.0 | Dipropylene glycol | 6.0 | Dipropylene glycol | 6.0 |
| Penetrant | 1,2-hexanediol | 2.5 | 1,2-hexanediol | 2.5 | 1,2-hexanediol | 2.5 |
| Surfactant | polyoxyethylene sorbitan monooleate | 1.5 | polyoxyethylene sorbitan monooleate | 1.5 | polyoxyethylene sorbitan monooleate | 1.5 |
| Water |  | 73.0 |  | 73.5 |  | 72.5 |

The amount of a typical fluid droplet for an ink formulation according to the disclosure may range from about 2000 to about 4000 picograms. Corresponding fluid droplet diameters may range from about 10 μm to about 20 μm.

Ink sets generally in accordance with the above formulations were tested in conventional ink jet printers to determine the drop mass, droplet velocity, and printing stability over a range of printing frequencies. All of the tests were conducted at 45° C. ink jet head temperature and 11 volts. The firing sequence for the cosmetic ink set was as follows: pre-fire pulse width 200 nsec; delay pulse width 800 nsec; main fire pulse width 470 nsec. The firing sequence for the conventional ink set was as follows: pre-fire pulse width 200 nsec; delay pulse width 800 nsec; main fire pulse width 450 nsec. The cosmetic ink sets described herein TABLE 2 were compared to conventional ink jet ink sets TABLE 3 as shown in the following tables.

TABLE 2

|  | 9 kHz Frequency | | 18 kHz Frequency | |
|---|---|---|---|---|
| Cosmetic Ink Set | Drop Mass (ng) | Velocity (m/sec) | Drop Mass (ng) | Velocity (m/sec) |
| Cyan Ink 1 | 2.96 | 8.8 | 3.49 | 9.6 |
| Cyan Ink 2 | 3.60 | 8.1 | 3.07 | 8.9 |
| Magenta Ink 1 | 2.91 | 8.6 | 3.53 | 9.4 |
| Magenta Ink 2 | 3.66 | 8.1 | 2.93 | 8.7 |
| Yellow Ink 1 | 2.93 | 8.8 | 3.66 | 9.6 |
| Yellow Ink 2 | 3.66 | 8.1 | 2.89 | 8.9 |

TABLE 3

|  | 9 kHz Frequency | | 18 kHz Frequency | |
|---|---|---|---|---|
| Conventional Ink Set | Drop Mass (ng) | Velocity (m/sec) | Drop Mass (ng) | Velocity (m/sec) |
| Cyan Ink 1 | 3.68 | 9.0 | 3.323 | 9.7 |
| Cyan Ink 2 | 3.36 | 9.3 | 3.83 | 10.1 |
| Magenta Ink 1 | 3.64 | 8.8 | 3.19 | 9.7 |
| Magenta Ink 2 | 2.85 | 9.2 | 3.76 | 9.9 |
| Yellow Ink 1 | 3.61 | 8.9 | 3.08 | 9.7 |
| Yellow Ink 2 | 2.77 | 9.3 | 3.73 | 10.0 |

As shown by the foregoing tables, the cosmetic ink set had a drop mass ranging from 2.91 to 3.66 ng at 9 kHz and from 2.89 to 3.66 ng at 18 kHz. This compared favorably with the drop mass of the conventional ink set that ranged from 2.77 to 3.68 ng at 9 kHz and from 3.08 to 3.83 ng at 18 kHz. The droplet velocity of the cosmetic ink set ranged from 8.1 to 8.8 m/sec at 9 kHz and from 8.7 to 9.6 m/sec at 18 kHz while the conventional ink set had droplet velocities of 8.8 to 9.3 m/sec at 9 kHz and from 9.7 to 10.1 m/sec at 18 kHz. Accordingly, the cosmetic ink set performed similarly to the conventional ink set with regard to droplet velocity.

An important feature of the cosmetic ink set according to the disclosure is the reliability of the ink set in an ink jet printer. A measure of the reliability of the ink set is its graininess score and its banding score after multiple (such as 8 passes) of the ink jet print head over a wiper after printing. The banding score looks for missing ink droplets which shows up as bands or lines across a printed page. A banding score of less than 0.15, such as from 0 to about 0.11 is suitable for most printing application. The cosmetic ink set described herein had a banding score of from 0.04 to 0.08.

The graininess score is used to determine misdirection clustering such that individual ink droplets can be detected on a substrate. An acceptable graininess score ranging from 0.1 to less than 1.2 for is acceptable. A graininess score above 1.3 is typically not acceptable for most printing applications. The cosmetic ink set according to the disclosure had a graininess score ranging from about 0.2 to about 1.03.

The foregoing ink set compositions may be useful in a variety of applications directed to decoration and/or enhancement of mammalian skin and/or nails. The methods of use for the compositions disclosed herein include, but are not limited to: 1) methods of applying a color cosmetic to skin; 2) methods of providing even skin tone; 3) methods of masking the appearance of vellus hair on skin; 4) methods of concealing blemishes and/or imperfections in human skin, including acne, age spots, freckles, moles, scars, under eye circles, birth marks, post-inflammatory hyperpigmentation; 5) methods of enhancing or modifying skin color such as lightening, darkening, making more pink, making more yellow, making less dull, making less ashy, making less orange, making more radiant; 6) methods of concealing vitiligo; 7) methods of decorating the skin and/or nails; and the like. When the cosmetic ink set is being applied to substantially non-porous surfaces, an ink receptive layer may be applied to the surface prior to printing. Ink receptive layers may include mixtures of pigments and fibers in admixture with a binder to provide a suitable ink receptive surface.

The cosmetic ink set described herein may be used in a hand-held micro-fluid printing device such as an ink jet pen 10 shown in FIG. 1. The pen 10 includes a body 12 that houses an ink cartridge, a rechargeable battery, ink jet print head, and a controller. The ink cartridge contains the cosmetic ink set described herein for full color printing. Ejection of ink droplets 14 from the pen 10 onto a substrate such as skin or nails is controlled by an activation switch 18 on the body 12 of the pen 10. A charging and ink jet head cleaning station 20 may be provided to recharge the pen 10 and clean the ink jet print head when the pen 10 is not in use. Other ink jet printing devices, including, but not limited to, conventional ink jet printers may also be used with the cosmetic ink set described herein.

It is contemplated, and will be apparent to those skilled in the art from the preceding description and the accompanying drawings, that modifications and changes may be made in the embodiments of the disclosure. Accordingly, it is expressly intended that the foregoing description and the accompanying drawings are illustrative of exemplary embodiments only, not limiting thereto, and that the true spirit and scope of the present disclosure be determined by reference to the appended claims.

What is claimed is:

1. A method of printing with cosmetic inks on human nails and skin comprising providing an ink jet pen and an ink set for full color thermal ink jet printing, the ink set consisting of:
    a) a cyan ink consisting of (1) a mixture of BRILLIANT BLUE and ACID BLUE 9 dye in an amount ranging from about 3.5 to about 4 wt. %; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 70 to about 75 wt. % water all based on a total weight of the cyan ink;
    b) a magenta ink consisting of (1) a mixture of ACID RED 33 AND ACID RED 52 dye in an amount ranging from about 2 to about 2.4 wt. %; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 70 to about 75 wt. % water all based on the total weight of the magenta ink; and
    c) a yellow ink consisting of (1) ACID YELLOW 23 dye in an amount ranging from about 5.8 to about 6 wt. %; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 69 to about 71 wt. % water all based on a total weight of the yellow ink;

wherein the ink set is devoid of non-cosmetically approved amounts of components; and ejecting the ink set from an ink cartridge containing the ink set in a predetermined amount onto the skin, fingernails or toenails of a person.

2. The method of claim 1, further comprising pre-coating nails with an ink receptive layer prior to printing on the fingernails or toenails.

3. A hand-held ink jet pen comprising a cyan, magenta and yellow ink set for full color printing on humans, the ink set consisting of:
    a) a cyan ink consisting of a a mixture of BRILLIANT BLUE and ACID BLUE 9 cyan dye in an amount ranging from about 3.5 to about 4 wt. %; .%; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 70 to about 75 wt. % water all based on a total weight of the cyan ink;
    b) a magenta ink consisting of a mixture of ACID RED 33 AND ACID RED 52 in an amount ranging from about 2 to about 2.4 wt. %; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 70 to about 75 wt. % water all based on a total weight of the magenta ink; and
    c) a yellow ink consisting of ACID YELLOW 23 dye in an amount ranging from about 5.8 to about 6 wt. %; (2) from about 12 to about 16 wt. % propanediol; (3) from about 5 to about 7 wt. % dipropylene glycol; (4) from about 2 to about 3 wt. % hexanediol; (5) from about 1 to about 2 wt. % polyoxyalkylene sorbitan monooleate; and (6) from about 69 to about 71 wt. % water all based on a total weight of the yellow ink;

wherein the ink set is cosmetically approved for printing onto skin, fingernails or toenails of a person and the ink set is devoid of non-cosmetically approved amounts of components.

4. The hand-held ink jet pen of claim 3, wherein a printed image from the ink jet pen has a banding score of less than about 0.09.

5. The hand-held ink jet pen of claim 3, wherein a printed image from the ink jet pen has a graininess score of less than about 1.2.

6. The hand-held ink jet pen of claim 3, wherein the polyalkylene sorbitan monooleate is selected from the group consisting of polyoxyethylene sorbitan monolaurate, polyoxyethylene sorbitan monostearate, polyoxyethylene sorbitan monooleate, and mixtures thereof.

* * * * *